United States Patent [19]
Brotman

[11] Patent Number: 4,778,466
[45] Date of Patent: Oct. 18, 1988

[54] NASAL PROSTHESIS

[76] Inventor: Morton Brotman, 3600 Labyrinth Rd.-A12, Baltimore, Md. 21215

[21] Appl. No.: 867,047

[22] Filed: May 27, 1986

[51] Int. Cl.⁴ .................. A61M 29/00; A61F 5/08
[52] U.S. Cl. ............................ 623/10; 128/342; 128/343; D24/33; D24/99
[58] Field of Search ............... 623/10; 128/342, 343; D24/33, 99

[56] References Cited
U.S. PATENT DOCUMENTS

| | | | |
|---|---|---|---|
| 1,597,331 | 8/1926 | Thurston et al. | 128/342 |
| 3,460,533 | 8/1969 | Plá | 128/342 |
| 3,710,399 | 1/1973 | Hurst | 623/10 |
| 4,414,977 | 11/1983 | Rezakhany | 128/342 |

Primary Examiner—V. Millin
Attorney, Agent, or Firm—Walter G. Finch

[57] ABSTRACT

An improved nasal prosthesis is disclosed. The improved nasal prosthesis is adjustable and therefore provides a single design which is adaptable to a variety of patients. The improved prosthesis includes an adjustable strut and adjustable rings.

9 Claims, 1 Drawing Sheet

NASAL PROSTHESIS

FIELD OF THE INVENTION

The present invention relates to an intranasal prosthesis and more particularly to an adjustable intranasal prosthesis which can be easily inserted and removed by the patient.

BACKGROUND OF THE INVENTION

Rhinologic surgeons are becoming increasingly aware of the importance of the nasal value region where nasal airway resistance is a problem. There has been an increased recognition that surgery to the nasal valve region can compromise the function of the nose. It is well known that injudicious surgery to the alar cartilage can result in alar collapse. Recent studies have proven that routine management of the osteocarfilagenous vault may damage the nasal airway, requiring further compensatory surgery.

There are various situations in which an intranasal prosthesis may be preferred to surgery. Some patients are adverse to surgery because of fear, anxiety or frustration due to prior procedures. In other patients, surgery is simply unnecessary or contraindicated. In yet other patients, temporary, intermittent or minimal symptomatology dictate that a prosthesis is preferred to surgery.

For the aforementioned types of patients a simple intranasal prosthesis will enhance the passage of air through the nasal valve region. However, the cost of such prosthesis is high because each prosthesis is fabricated to a particular patient's nostril. In other words the ordinary prosthesis is a custom made device.

SUMMARY OF THE INVENTION

Thus, it is an object of the present invention to provide an improved nasal prosthesis which is easy for the patient to insert and remove.

It is a further object of the present invention to provide an improved nasal prosthesis which is inexpensive.

It is yet another object of the present invention to provide an improved nasal prosthesis which is fully adjustable and therefore providing a single design which is suitable to more than one patient.

Accordingly an improved nasal prosthesis is provided which has two adjustable rings and one or more adjustable struts. The struts may be inwardly bent to avoid contact with nasal tissues.

DESCRIPTION OF THE PREFERRED EMBODIMENT

The improved nasal prosthesis consists of two adjustable rings and one or more adjustable struts. The device may be made from non-reactive materials such as stainless steel and cadmium free silver solder.

Figure 1:
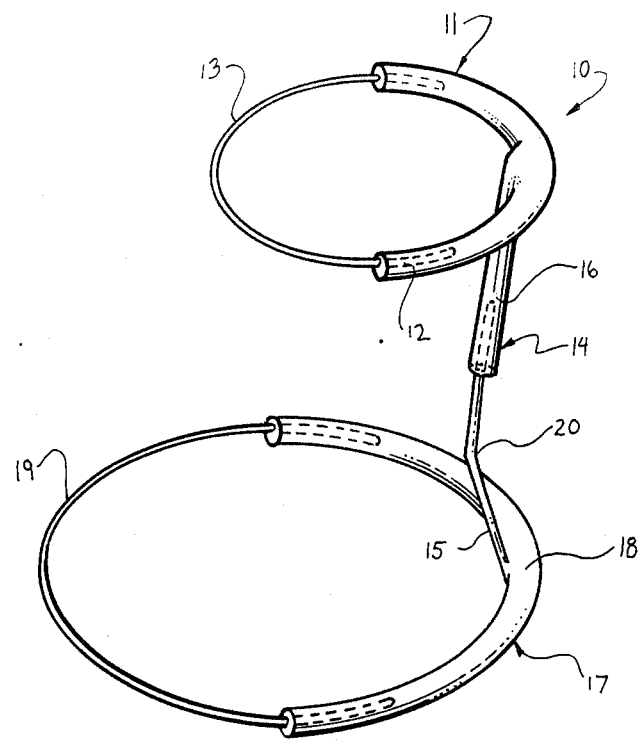
FIG. 1 is a perspective view of the improved prosthesis.
Figure 2:
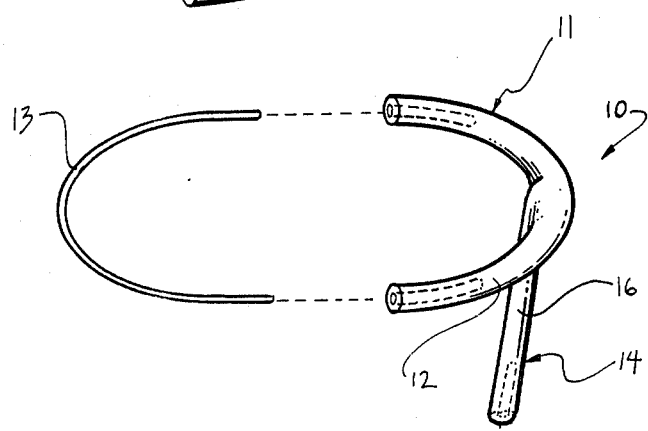
FIG. 2 is an exploded perspective of the improved nasal prosthesis showing the individual components of the device of the present invention.
Figure 2:
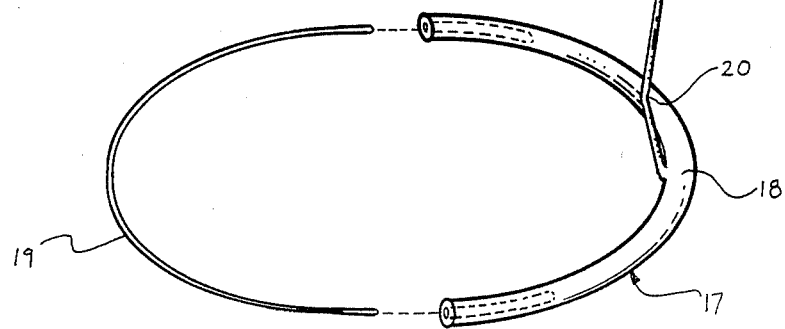

FIGS. 1 and 2 shows the improved nasal prosthesis 10. The prosthesis has a small top ring 11, which consists of a hollow member 12 and a narrow member 13. The narrow member 13 fits snugly yet slidably in the hollow member 12. A strut 14 is attached to the outer surface of the top ring 11. The strut has a male member 15 and a sleeve 16. Either the sleeve 16 or male member 15 may be bent at 20. In FIG. 2 it may be seen that the male member 15 is bent at 20 so to prevent excess contact with nasal tissue.

The sleeve 16 snugly yet slidably receives the male member 15. The male member 15 is attached to the outer surface of a larger bottom ring 17. The bottom ring is somewhat larger than the top ring 11 and consists of a hollow element 18 and a narrow element 19. The narrow element 19 fits snugly yet slidably within the hollow narrow element 19.

Thus the rings 11 and 17 are extensible and the strut 14 is similarly extensible or telescopic. Two struts may be provided where it would be advantageous.

The prosthesis 10 is inserted by the patient by first moistening the vestibular skin. The top ring 11 is then inserted. The little finger is then used to push the prosthesis 10 inward until the bottom ring 11 cannot be seen. The small ring 11 should be located in the plane of the nasal valve area. The larger bottom ring 17 is designed to be large enough so that it cannot easily pass the nasal valve and fall into the nose.

Accordingly it will be appreciated by those skilled in the art that various modifications may be practiced in conjunction with the improved nasal prosthesis without departing from the spirit of the present invention.

What is claimed is:

1. In a nasal prosthesis, the improvement comprising an adjustable top ring partially hollow, an adjustable bottom ring partially hollow, and at least one adjustable strut connected to said top and bottom adjustable rings and cooperating between said top ring and said bottom ring.

2. In a nasal prosthesis as recited in claim 1, wherein said at least one adjustable strut is attached at its ends to the interior of said top ring and to the interior of said bottom ring.

3. In a nasal prosthesis as recited in claim 2, wherein said one adjustable strut further comprises a male member and a sleeve for receiving said male member.

4. In a nasal prosthesis as recited in claim 3, wherein said one adjustable strut is bent inwardly.

5. In a nasal prosthesis as recited in claim 4, wherein said adjustable top ring further comprises a hollow member and a narrow member, said narrow member snugly yet slidably received by said hollow member.

6. In a nasal prosthesis as recited in claim 5, wherein said adjustable bottom ring further comprises a hollow element and a narrow element, said narrow element snugly yet slidably received by said hollow member of said second adjustable bottom ring.

7. In a nasal prosthesis as recited in claim 6, wherein said sleeve of said strut is joined to said hollow member of said top ring and wherein said male member of said same strut is fixed to said hollow element of said bottom ring.

8. In a nasal prosthesis comprising an adjustable top ring, said top ring consisting of a hollow member and a narrow member snugly yet slidably received by the hollow member; an adjustable strut consisting of a sleeve attached to the outer surface of said hollow member and a male member snugly yet slidably received by said sleeve, said male member being bent inwardly; and an adjustable bottom ring consisting of a hollow element and a narrow element, said narrow element of said bottom ring snugly yet slidably being received by said hollow element of said bottom ring; with said male member of said strut being fixed to the outer surface of said hollow element of said bottom ring.

9. In a nasal prosthesis as recited in claim 8, wherein said adjustable bottom ring is larger than said adjustable top ring.

* * * * *